(12) United States Patent
Strattner

(10) Patent No.: US 11,406,394 B2
(45) Date of Patent: Aug. 9, 2022

(54) TOURNIQUET WINDLASS DEVICE

(71) Applicant: Christopher Strattner, Pearl River, NY (US)

(72) Inventor: Christopher Strattner, Pearl River, NY (US)

( * ) Notice: Subject to any disclaimer, the term of this patent is extended or adjusted under 35 U.S.C. 154(b) by 807 days.

(21) Appl. No.: 16/363,824

(22) Filed: Mar. 25, 2019

(65) Prior Publication Data

US 2019/0216471 A1     Jul. 18, 2019

Related U.S. Application Data

(62) Division of application No. 15/185,653, filed on Jun. 17, 2016, now Pat. No. 10,278,709.

(51) Int. Cl.
*A61B 17/132* (2006.01)
*B43K 29/00* (2006.01)

(52) U.S. Cl.
CPC .......... *A61B 17/1327* (2013.01); *B43K 29/00* (2013.01)

(58) Field of Classification Search
CPC .. A61B 17/132; A61B 17/1327; B43K 25/02; B43K 25/022
See application file for complete search history.

(56) References Cited

U.S. PATENT DOCUMENTS

| | | |
|---|---|---|
| 3,307,551 A | 3/1967 | Violet, Jr. |
| D286,648 S | 11/1986 | Perrin et al. |
| 4,821,720 A | 4/1989 | Hajduch |
| 5,027,800 A | 7/1991 | Rowland |
| D506,780 S | 6/2005 | Nakazawa |
| 7,125,186 B1 | 10/2006 | Stokes |
| 8,652,164 B1 | 2/2014 | Aston |
| D701,564 S | 3/2014 | Moon |
| D709,949 S | 7/2014 | Fleming |
| D728,867 S | 5/2015 | Hui |
| D740,365 S | 10/2015 | Vadenne |
| 9,149,280 B2 | 10/2015 | Croushorn et al. |
| D745,089 S | 12/2015 | Cohen |
| 2010/0104344 A1 | 4/2010 | Gitman et al. |
| 2015/0257767 A1 | 9/2015 | Henderson |
| 2016/0302799 A1* | 10/2016 | Esposito ............ A61B 17/1322 |
| 2016/0367262 A1* | 12/2016 | Burke ................ A61B 17/1322 |

FOREIGN PATENT DOCUMENTS

| | | |
|---|---|---|
| GB | 15603 | 10/1916 |
| GB | 2505172 A | 2/2014 |
| WO | 2015119774 A1 | 8/2015 |
| WO | 2015119968 A1 | 8/2015 |

OTHER PUBLICATIONS

Boker Manufacturer, https://www.boker.de/us/tactical-pen/09BO097.html (downloaded Jan. 25, 2016).

* cited by examiner

*Primary Examiner* — Sarah W Aleman
(74) *Attorney, Agent, or Firm* — Dorf & Nelson LLP; Scott D. Locke, Esq.

(57) ABSTRACT

A tourniquet windlass device is provided with a writing functionality. The device may be designed such that it may be used with an improvised constricting band such as a necktie or other fabric.

20 Claims, 2 Drawing Sheets

TOURNIQUET WINDLASS DEVICE

CROSS-REFERENCE TO RELATED APPLICATION

This application is a divisional application of pending U.S. patent application Ser. No. 15/185,653, filed Jun. 17, 2016. The entire disclosure of the aforementioned patent application is hereby incorporated by reference into the present disclosure.

FIELD OF THE INVENTION

The present invention relates to the field of tourniquets.

BACKGROUND OF THE INVENTION

Tourniquets are used to stop uncontrollable bleeding or extremely difficult to control bleeding of an injured person. By using a tourniquet, blood flow to a limb can be stopped by constricting all blood vessels within the limb to which it is applied. Healthcare professionals and other persons who are trained in first aid know that bleeding can be a serious condition, and failing to stem major bleeding can be life-threatening within minutes of injury. Methods other than using tourniquets e.g., applying direct pressure and elevation of a bleeding body part, can often be ineffective in instances of sudden massive bleeding, and the failure to achieve complete cessation of blood flow may result in other adverse effects for a victim including continued bleeding and compartment syndrome (where continued blood flow past an ineffective tourniquet causes "pooling" of blood in an extremity thereby allowing potentially lethal toxins to form within the body). Because of the potential for mortality and morbidity in victims with serious bleeding, it is critical that the tools to create an effective tourniquet are readily available.

Tourniquets typically comprise two parts, a windlass and a constricting band. The constricting band is used for the purpose of narrowing blood vessels such as arteries, veins, capillaries, or pluralities of one or more of them to the point of blocking most or all blood flow. A person who applies the tourniquet, who might or might not be the injured person himself or herself, wraps the constricting band around the injured limb and tightens it.

In order to facilitate the tightening of the constricting band around the limb, often the person applying it will also loop the constricting band around a windlass device. Thus, just prior to constricting the blood vessels in a limb, the constricting band may have a contiguous loop or be modified or tied to form a contiguous loop, i.e., by tying two ends of a piece of fabric or rope. By rotating the windlass, one will introduce twists into the constricting band, thereby causing the portion of the constricting band around the injured limb to tighten and thereby to completely constrict the blood vessels in that limb.

As a practical matter, most persons do not need a tourniquet on most journeys or outings. Consequently, there is a temptation not to bring any device that may be used as a windlass. Unfortunately, too often persons in need of a tourniquet find themselves without easy access to a windlass. The present invention addresses this issue by providing a device that may be used as an effective windlass and that has an additional utilitarian function that increases the likelihood that it will be brought on a journey or on an outing.

SUMMARY OF THE INVENTION

The present invention provides a device for use as a windlass in a tourniquet and methods for using the device. The device may be used to decrease or to stop the flow of fluid, e.g., blood through a tube or vessel such as an artery or a vein or pluralities of one or more of them in a limb. This device, which may have at least two functionalities that enable the device to serve as an effective windlass and e.g., a writing instrument, there may be an increased likelihood that a person such as an EMT, healthcare professional, girl scout leader, boy scout leader, counselor, camper, lifeguard, armed services member or other person, will bring it with him or her. Consequently, there is an increased likelihood that he or she will be prepared in case he or she needs to apply a tourniquet.

According to a first embodiment, the tourniquet windlass device comprising a clip and a housing, wherein the housing comprises: (1) a first region, (2) a second region, wherein the second region has a surface that contains knurling, and (3) a third region, wherein the third region is associated with the clip, wherein the second region is narrower than the widest portion of the first region and narrower than the widest portion of the third region According to a second embodiment, the present invention is directed to a tourniquet windlass device comprising: (A) a clip; and (B) a housing, wherein the housing comprises, consists essentially of, or consists of: (1) a first region, (2) a second region, wherein the second region has a surface that contains knurling, and (3) a third region, wherein the third region is associated with the clip (e.g., affixed to a clip or part of a structure that includes a clip), and the clip is configured to secure at least a portion of a restricting band when said restricting band is in use in a tourniquet, wherein the second region is located between the first region and the third region, and the second region is narrower than the widest portion of the first region and narrower than the widest portion of the third region. Optionally, the device further comprises a writing element, wherein the writing element comprises at least one of ink, graphite, lead, and chalk and the writing element is associated with at least the first region. In some embodiments, the first region, the second region, and the third region are contiguous, the clip extends from the third region, and the clip and housing are made as a part of a single molding process and made from the same material.

According to a third embodiment, the present invention is directed to a method for constricting a tube or a vessel through which fluid flows, thereby decreasing fluid flow or stopping fluid flow completely. By way of a non-limiting example, the vessel may be a blood vessel such as an artery or vein within a limb, and the fluid may be blood or other bodily fluids, e.g., lymph. The method comprises: (a) wrapping a constricting band around a limb, (b) associating a device of the present invention with the constricting band; (c) twisting the device, thereby reducing blood flow; and (d) securing the constricting band in the clip of the device, by e.g., sliding a portion of the constricting band past a retaining element of the clip.

Through one or more of the various embodiments of the present invention, a user may take a device described herein and use it with another item that serves as a constricting band, e.g., a common necktie or another fabric material that forms, or from which one may form a loop, or a belt, as a tourniquet. A constricting band may also be referred to as a restricting band.

DETAILED DESCRIPTION OF THE INVENTION

Figure 1:
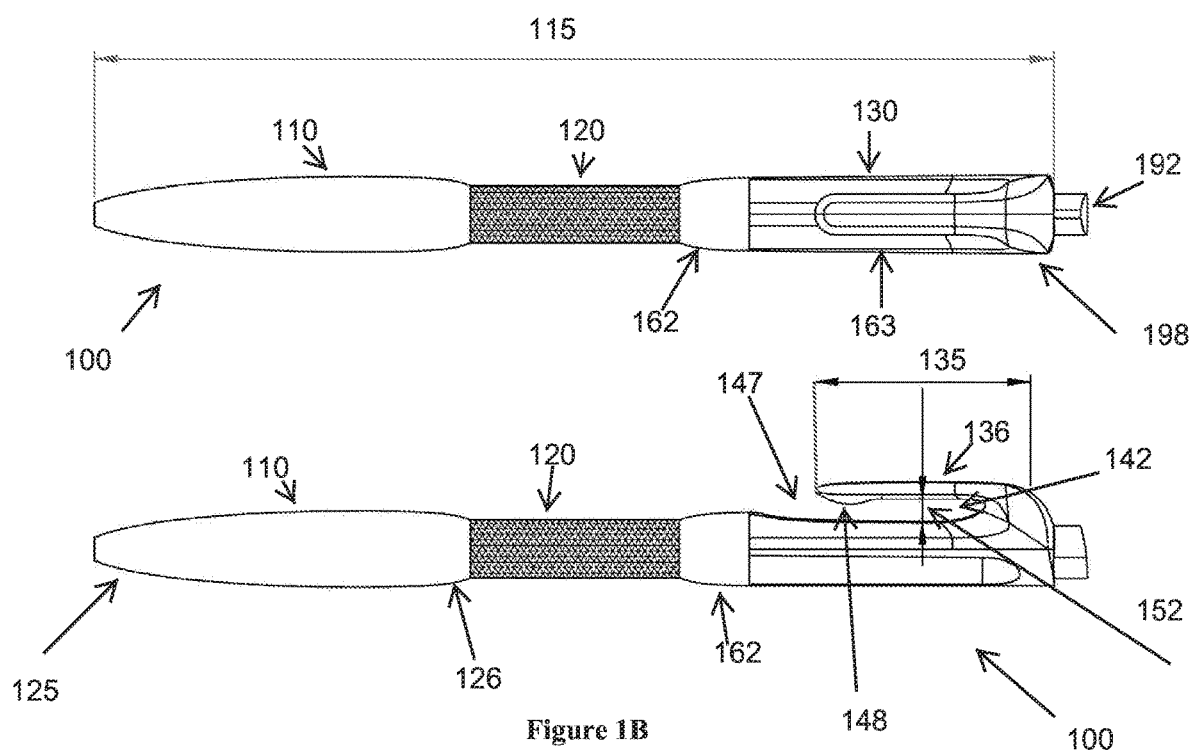
FIG. 1A is a representation of a device of the present invention.
FIG. 1B is another view of the device of FIG. 1A.
Figure 2:
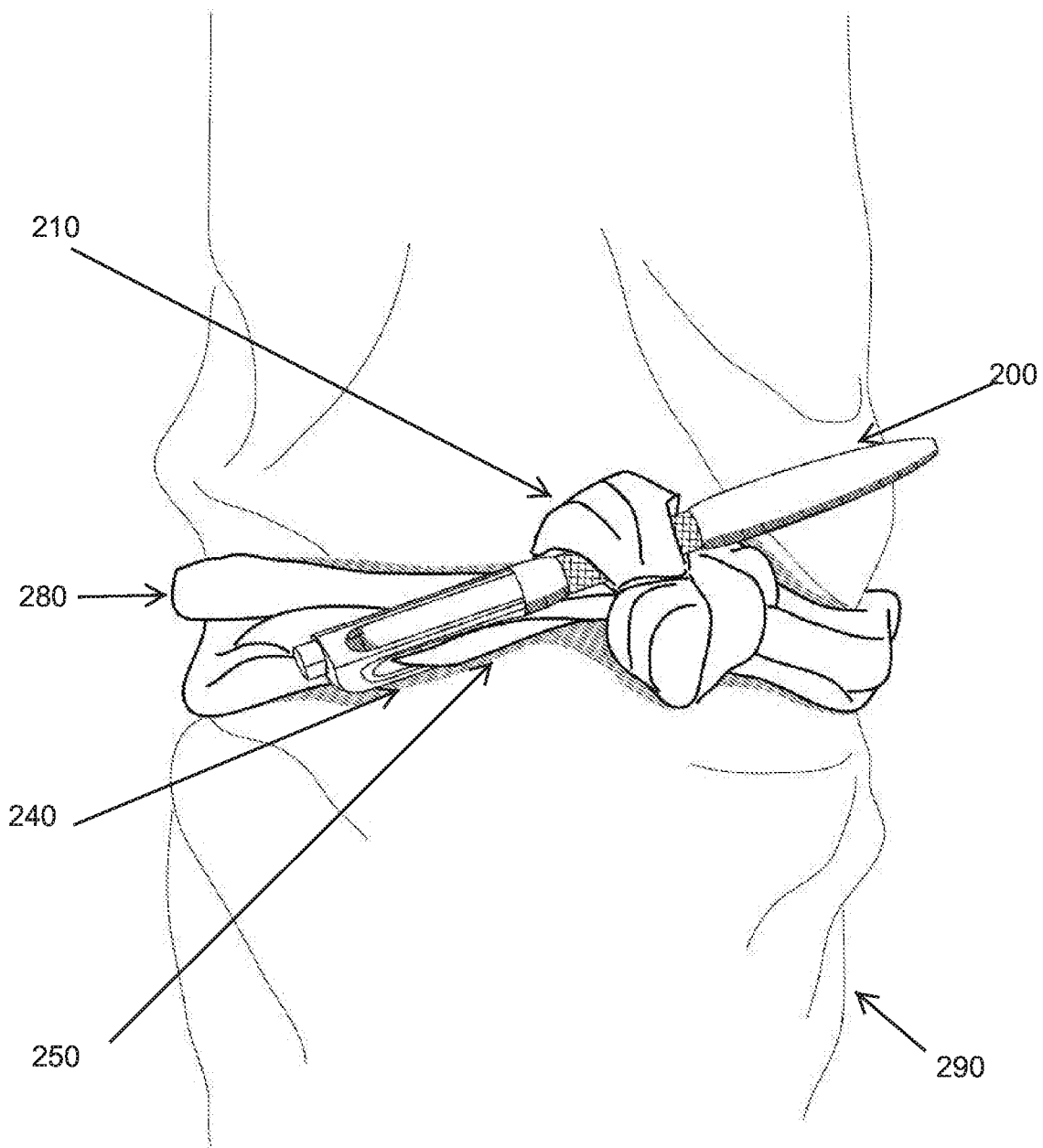
FIG. 2 is a representation of a device of the presenting invention in use with a constricting band that is twisted around a limb.

Reference will now be made in detail to various embodiments of the present invention, examples of which are illustrated in the accompanying figures. In the following detailed description, numerous specific details are set forth in order to provide a thorough understanding of the present invention. However, unless otherwise indicated or implicit from context, the details are intended to be examples and should not be deemed to limit the scope of the invention in any way. Furthermore, headings are provided for the convenience of the reader and are not intended to be and should not be construed as limiting any of the embodiments described herein.

As used in the description and throughout the claims, the meaning of "a," "an," and "the" include plural references unless the context dictates otherwise.

Additionally, throughout this disclosure, numerical values are provided. Unless otherwise stated or suggested by context, they are provided as examples and should be construed in light of reported significant digits and by applying ordinary rounding techniques.

Further, the recitation of ranges of values herein is merely intended to serve as a shorthand method of referring individually to each separate value falling within the range. Unless otherwise indicated herein, each individual value is incorporated into the specification as if it were individually recited herein. Additionally, the use of any and all examples and language of "such as" or "including" provided with respect to certain embodiments herein is intended merely to illuminate better the invention and does not pose a limitation on the scope of the invention.

According to a first embodiment, the present invention is directed to a tourniquet windlass device comprising a clip and a housing that is associated with or affixed to or part of a structure that contains the clip and optionally, a writing element. For convenience and to illustrate the invention, the term "housing" is used to refer to the portion of the device that is configured to store or to house a writing element, but does not include the portion of the device that forms the clip. In some embodiments, the device 100 is, for example, between 100 and 300 mm in length or between 125 and 250 mm in length or between 135 and 225 mm in length.

Housing

The housing has three regions that are configured to allow the device to function efficiently as a windlass of a tourniquet and comprises, consists essentially of, or consists of, or is made from a sufficiently strong material so as to withstand the twisting force necessary to occlude blood, e.g., a metal or metal alloy or sufficiently strong plastic or a combination thereof. By way of a non-limiting example, the housing and clip may be made from a single material such as a stainless steel or anodized aluminum, or a sufficient strong plastic polymer. One may use molding technologies to manufacture the device, and after one manufactures the device, one may add a writing material with its storage and dispensing elements, (e.g., tube carrying ink and ball point) as well as any structure for activation of a writing element.

For reference, the housing may be described as having: a first region 110, a second region 120 and a third region 130. The second region is located between the first region and third region. In some embodiments, the three regions may be contiguous without any intervening structure. Transitions between these regions may be gradual or abrupt, uniform or non-uniform, and regular or irregular.

In one non-limiting embodiment, the device has the following dimensions: (1) a first region that contains (i) a tapered tip that is 24 mm long, has circular cross-sections, is capable of being unscrewed in order to insert a writing element and is distal from the second region, (ii) a cylindrical (tubular) section that has a uniform circular outer diameter of 11 mm and is 25 mm long and is between the tapered tip and tapered end of the first region, and (iii) a tapered end (narrower proximal to the second region) that is 12 mm long, has circular cross-sections, and is between the cylindrical section and the second region; (2) a second region that abuts the first region, has a uniform outer diameter of 9.5 mm and knurling over its entire surface; (3) a third region that abuts the second region and has (i) a transition region that is tapered (narrower proximal to the second region) and expands to 11 mm in diameter and is 12 mm long, (ii) a leverage region that has a front side that slopes away from the transition region to form a mouth between an end of a clip and the leverage region; and (iii) a left side scoop region that is 37 mm long and a right sight scoop region that is 37 mm long, with the scoop regions being planar, concave or a combination thereof and the portions of the leverage region that are not the scoops or mouth or cavity are rounded or planar or a combination thereof; (4) a clip with a bulging retaining element (e.g., a nub) on the inner side of the clip, wherein the clip is 30 mm long on the outside and 25 mm long from its retaining element to the part of the cavity formed by the clip that is distal to the retaining element; (5) a cavity formed by the clip that is 3.3 mm at its widest (from clip to front of leverage region); and (6) a mouth that is 8.5 mm, which corresponds to the distance from the tip of the clip to the thickest part of the leverage region. The length between the scoop and the end of the device not including any plunger for activating a writing element is 4 mm long, and if a plunger is present, the exposed part may be 5 mm long. An internal shaft of the housing may have a uniform diameter of 6 mm that spans the length of the housing.

The first region 110 is configured to house and or to be associated with a writing element. Optionally, one or both of the ends of the first region are tapered 125, 126. The configuration of the tapering at each of the two ends of the first region may be the same or different. The tapering at the end of the first region that is distal from the second region is common in many writing instruments today. The tapering at the end of the first region that is proximal to the second region is where there is a transition between the first region and the second region. In some embodiments, other than any tapering that is present, the first region is a regular shape that is tubular or substantially tubular with a substantially uniform or uniform outer diameter and each of the cross-sections of the first region are symmetrical over 360 degrees and are circular. In other embodiments, the first region may have another regular or irregular shape and, not including the tapered region at the tip, have an outer diameter that is not tubular but has a more gradual slope or curvature than the tapered regions. Additionally, the outer surface of the first region may be smooth or textured. In some embodiments, the first region is 30 mm to 60 mm long and has a widest width of 9 mm to 13 mm, and a narrowest outer diameter at the end where a writing element may emerge. In some embodiments, this narrowest diameter is e.g., 6-8 mm. Therefore, over the entire first section, the out diameter, may, for example, be 6-13 mm.

The second region 120 may be tubular or have another regular or irregular shape and optionally, may be designed to have one or more concave regions or have a uniform outer diameter and be cylindrical. In some embodiments, there is a concave region that spans 360 degrees around the device. When the concave region spans 360 degrees around the device, the housing may have the gross shape of an hourglass. In other embodiments, the concave region spans less than 360 degrees around the device. The inclusion of a concave region may assist in preventing slippage of the constricting band. To the extent that the second region has one or more concave regions, the region or regions that are concave may span the length of the second region or less than the length of the second region, e.g., at least 50%, at least 60%, at least 70%, at least 80%, or at least 90% of the length of the second region. For example, they may span from 60% to 90% of the length of the second region.

Over part or the entire second region, there may be texturing and e.g., the second region may contain knurling. Knurling refers to a pattern of depressions or raised areas or a combination thereof, e.g., surfaces that are roughened, ribbed, scalloped, grooved, or otherwise textured. Knurling or other texturing may be included in order to prevent travel of the constricting band along the windlass shaft or roll of the windlass shaft. When there is knurling, it may be over all or part of the outer surface second region, e.g., over at least 50%, at least 60%, at least 70%, at least 80% or at least 90% of the outer surface of the second region. Further, in some embodiments, the knurling extends to part or all of one or both of the first region and the third region. In other embodiments, it is present only over part or some of the second region. Alternatively or additionally, the second region may contain a coating or cover that is made of a material that has a greater coefficient of static friction than one or both of the first region and the second region. The knurling region may cover the mid-point of the length of the device, and in some embodiments, is centered over this mid-point. Preferably, the center of gravity of the device is in the second region at or near the midpoint of the knurling region. The presence or absence of knurling is independent of the presence or absence of a section of the second region being concave.

In some embodiments, the second region is solid. In other embodiments, the interior of the second region has a space (e.g., a bore) that is contiguous with a space within the first region and configured to allow storage of some the writing substance and a container for it. Optionally, if this space is present, it also extends through at least part, if not all, of the third region.

In some embodiments, the second region has a width of e.g., an outer diameter when the second region is a cylinder, of 8 mm to 11 mm or 9 mm to 10 mm and a length of 25 mm to 35 mm or 28 mm to 32 mm.

Associated with the third region 130 is a clip 136 as described below. In some embodiments, the third region is tubular or substantially tubular in shape. Additionally, in some embodiments, like the second region and the first region, each of the cross-sections of the third region may be symmetrical over 360 degrees or symmetrical over the 360 degrees except for the clip. In other embodiments, the outer sides of the third region render it symmetrical over less than 360 degrees, e.g., along one plane (e.g., a plane that bisects the length of the clip) and thus is not circular in cross-section. In some embodiments, the third region is configured to allow for efficient turning of the device itself.

The inner configuration of the third region and second and first regions may, for example, contain a contiguous bore in order to allow for the placement of a storage tube in a manner that allows it to be coupled to a retraction mechanism at the end of the third region. Thus, the writing element of the windlass may be retractable. Activation of the retraction mechanism may, for example, be through a push button at the top of the device, and optionally, there may be a spring within the device.

In some embodiments, the third region may, for example, be symmetrical along only one plane. This plane, which is used for illustrative purposes and does not describe a physical structure, may bisect the length of the device, including the clip. In these cases, the third region may have (i) a transition region 162 and (ii) a leverage region 163. The transition region is between the second region and the leverage region. The transition region may, in some embodiments, abut the second region on one end and abut the leverage region on the other end. The transition region may, for example, have a regular (e.g., tubular) or irregular cross-section or be partially or entirely tapered with it being narrower proximate to the second region. Furthermore, it may be textured or non-textured on its surface. At its widest, it may be wider than the widest portion of the second region, and in some embodiments, the entire transition region is wider than the second region or at least as wide as the second region.

The leverage region may contain one or more areas that are planar, or concave or a combination thereof, and the clip may be shorter than, the same size as, or larger than the entire leverage region. Within the leverage region, there may be one, two, three, or more planar sections or concave sections, or sections that are partially concave and partially planar. These sections allow a user to exert torque more easily on the windlass device than in the absence of them, i.e., when they would otherwise be tubular or cylindrical. These sections may be referred to as a scoop, regardless of their configurations. The phrase "leverage region" is used for convenience, and within this region is a configuration that allows a user to have greater leverage when turning the device.

For illustrative purposes, the leverage region may be viewed as having or comprising a front side, a rear side, a left side and a right side, each which may be partly or completely planar or concave or a combination thereof, and optionally, at least as long as a user's thumb. By having planar and/or concave sections of side regions, there are convenient places for a user to rest his or her thumb and/or fingers when turning the windlass and tightening the constricting band. In some embodiments, the left side of the third region is the mirror image of the right side of the third region. The third region may also have a rear side that connects the left side region and the right side region, and a front side connects to the left side of the third region and the right side of the third region. The clip 136 extends from the housing in a manner such that a space or cavity 142 is defined between it and the front side of the third region of the housing. In some embodiments, the clip is shorter than the leverage region. In other embodiments, the clip is the same length as the leverage region. In still other embodiments, the clip is longer than the leverage region, but shorter than the entire third region.

As noted above, the planar or concave surfaces (or surfaces that are combinations thereof) may, for example, be on the right side and the left side of the leverage region. In some embodiments, they are in parallel planes or substantially parallel planes. (When a section is concave, the plane for which the issue of a parallel nature is examined may be defined as the plane that touches all points on the upper edge of the concave surface that forms the section.) In other embodiments, they are in non-parallel planes. E.g., the left side region and the right side region are each 30 degrees to 70 degrees or 40 degrees to 60 degrees, e.g., 50 degrees from the theoretical vertical plane that bisects the front and rear side. In these instances, the distance between the edges of the right side and left side that come into contact with the rear side is smaller than the distance from the edges of the left side and right side that are distal from the rear side, i.e., those connected by the front side.

In the embodiment described in the previous paragraph, the third region has one plane of symmetry. In some embodiments, only one of the right side or the left side comprises a planar, concave or combined planar/concave region, and thus the third region has no planes of symmetry. In either of these embodiments, the first region and second region may each independently have a plurality of axis of symmetry and each cross-section may have uniform radius exclusive of any knurling.

In some embodiments, the front side of the leverage region is partially or completely planar or partially or completely rounded, and it may be a regular or an irregular shape and smooth or structured and form a cavity with the clip. In some embodiments, over the third region, as one moves away from the locations proximal to the second region (transition region), the cross-sections change from circular and uniform over 360 degrees to non-circular and not symmetrical over any planes or symmetrical over only one plane. In the region that is symmetrical over one or no planes, the distance from the rear side to the front side may be less than the largest diameter over a portion of the third region in which there is a uniform cross-section (the transition region).

In some embodiments, when the left and right sides of the leverage region are planar, concave, or a combination thereof, there may be side between each of the left and right sides, and the cavity forms portion of the front side. These transitions regions may be planar, concave, convex, or another regular or irregular shape. Further, between the cavity and the tip of the device may be a region 198 that allows for transition to the clip 136.

In some embodiments, the left side region that is or comprises a section that is planar, concave or a combination thereof, and the right side region that is or comprises a section that is planar, concave or a combination thereof, each span less than 90% of the length of the third region, less than 80% of the length of the third region, less than 70% of the length of the third region, or less than 60% of the length of the third region. In some embodiments, each of these sections runs the length of 30% to 80% or 40% to 70% of the third region.

In some embodiments, the front region of the leverage region slopes away from the transition region 147 at the mouth. This slope continues until to the lowest point, which is under the clip and continues with a surface that is either planar or concave or a combination thereof and may have a reduced slope. From the lowest point, the surface may be flat or slope upward to the portion of the cavity that is distal to the retaining element.

In some embodiments, the width of the transition region is from 9 mm to 13 mm front to rear and side to side. At its widest, it may be the same width as the widest part of the first region. Further, in some embodiments, exclusive of the clip, no cross-section diameter of the device is wider than 9 mm to 13 mm.

Clip

As noted above, the device also contains a clip 136. The clip may be designed to define a space that is larger than a corresponding space in a standard pen and/or the clip is stronger than clips associated with standard pens. The clip defines a space, i.e., the cavity 142, that is large enough to accommodate a sufficient amount of material of the restricting band to hold the device in place and to prevent unwinding. Two parameters may be used to define the cavity that the clip and device create. First, there is the distance between the third region and the clip, which is the width of the cavity. Second, there is the distance from the retaining element to the portion of the cavity distal to the retaining element, which is the depth of the cavity.

The cavity may for example, be 3 mm to 4 mm wide 152 and 22 mm to 40 mm deep. In some embodiments, the clip is at least 25 mm deep, at least 30 mm deep or at least 35 mm deep. Additionally, in some embodiments, the clip is 5 mm to 9 mm or 6 mm to 8 mm, e.g., 7.5 mm wide from left to right.

In some embodiments, the clip is flexible. The flexibility allow for the sliding of the constricting band into the space defined by the clip. In some of these embodiments, the clip articulates with a hinge. The hinge may, for example, be located at or near where the clip associates with the third region. In other cases, it is rigid.

The retaining element 148 is the portion of the clip that defines the shortest distance between the front side of the third region and the portion of the clip that is closer to the second region than is the deepest part of the clip. The retaining element may, for example, have a nub that causes it to create a channel with the leverage region that is e.g., a width that is 0.5 mm to 1.5 mm narrower than the cavity. The nub may be located at or near an end of the clip that is distal to where the clip extends from the third region. In some embodiments, due to the flexibility of the material that forms the clip or its method of attachment to the surface of the top of the third region, this space is expandable by up to 10% or up to 20%. In some embodiments, the space at the retaining element of the clip is preferably at least 1.25 mm, at least 1.5 mm or at least 2 mm, e.g., 1.25 mm to 2 mm or 1.5 mm to 2.5 mm. In other embodiments, the clip is not flexible, and as described more fully below, manipulation of the constraining band allows it to slide or be slid past a nub of it and be held in place by it.

In one non-limiting example, the device is 137.68 mm from end to end, not including any depressable element 192 for activating a writing mechanism. The clip is 31.02 mm in length, the leverage region is 9 mm front to rear, the gap between the first region and the clip is 3.27 mm at a location not beneath the retaining element, and the clip is 1 mm thick. The largest cross-section of the device, including a clip, may, for example, be less than 14 mm, e.g., is 13.23 mm.

In some embodiments, the clip is made from the same materials and within the same molding as the housing, e.g., metal, a metal alloy, or a strong plastic or a combination thereof. Thus, the clip extends from the third region of the housing. In other embodiments, the clip is made from a different material and associated with the housing by an adhesive material such as a glue, cement or epoxy or by a physical force exerted on a ring that extends from the clip and is located between or around two pieces of the housing.

When the device is not in use as a windlass tourniquet or as a writing instrument, the clip may be used to secure the device in a pocket or to an article of clothing or an accessory.

Writing Element

As persons of ordinary skill in the art will recognize, the combination of the writing element and the structural features that allow the device to function as a writing instrument render the device desirable for persons who need to balance the weight and cumbersomeness of carrying multiple devices with the need to have a minimum number of functionalities within the set of devices that they carry. Thus, although a person could remove the writing element from the device, and the device would remain within the scope of the present invention as a windlass, in doing so, the person would not achieve the benefit of the efficiency of carrying a device with a plurality of functionalities.

The writing element is associated with at least the first region of the housing. It may, for example, be retractably housed within the first region, or within the first region and second region, or within the first region, the second region, and the third region. Alternatively, the writing element may be affixed to an end of the first region and/or not retractable. When not retractable, optionally, the device may be designed such that a portion of the writing element extends into or through the first region, or the first region and second region, or within the first region, the second region, and the third region.

By way of example, the writing element may comprise at least one of ink, graphite, lead, and chalk. Persons of ordinary skill in the art will recognize that the term ink includes but is not limited to ink that is typically found in ball-point pens, magic markers, ink-paint pens, and felt tip pens.

The writing element may include the substance that is to be used for writing, as well as any storage container, e.g., a plastic tube and/or applicator or dispenser, e.g., ball of a ball point pen. In some embodiments, the writing element is retractable and the device contains a click plunger mechanism and optionally a spring to reveal the writing element, which may, for example, comprising an ink cartridge. In other embodiments, the device is configured to release the ink cartridge, and to allow for replacement of it.

In some embodiments, a spring and release mechanism is included in order to allow for access to the writing element. The spring and release mechanism may be activated by an activator 192, which may also be referred to as a plunger.

By way of non-limiting examples, Parker Standard or Fisher Space ink cartridges may be used as part of the writing element.

Constricting Band

A constricting band is the material that will be wrapped around an injured or bleeding subject's limb in order to restrict and preferably occlude blood flow. It may or may not be elastic, and it may or may not have an additional use. One of the advantages of the present invention is that items that a user of a tourniquet would otherwise have present, may be used. For example, one may use fabric that a person would already otherwise carry or wear, e.g., a necktie, a belt, or an appropriately sized other piece of clothing or material that is long enough to be wrapped around a limb yet small enough to be used with a device of the present invention, i.e., fit within the clip. If the restricting band is not ordinarily a loop, and instead it has a free-end, e.g., is linear, then the ends may be tied together by a knot, thereby creating a loop.

Alternatively, one could use other materials as the constricting band. These materials include but are not limited to ropes, cords, laces, and cables.

Furthermore, one could carry a kit that contains a device of the present invention and a constricting band.

Alternative Embodiments and Additional Features

Within the scope of the present invention is the inclusion of one or both of an LED or halogen light and a laser, though in some embodiments neither of these elements is present. The light and/or laser, if present, may be in addition to or instead of the writing element described above at the locations described above for the writing element or at other locations.

If the LED or halogen light or the laser is present in addition to the writing element, it may, for example, be located in a light or laser structure that is affixed to the outside of the first region. In some embodiments, the light and/or laser may be located within the third region. If there is a light or laser, it preferably has an actuating mechanism to turn it on and off. Further, preferably there is a power supply such a battery that can power the light and/or laser.

In another embodiment, the device comprises a stylus. As persons of ordinary skill in the art are aware, a stylus may be used with computer touchscreens. The stylus may be in addition to or instead of the writing element described above. When used instead of the writing element, it may be located in any of the locations described above in which the writing element may be located, and it may be retractable or permanently accessible as described above. When a device includes a stylus in addition to a writing element, the stylus may be affixed to the outside of the device and, for example, be less than or equal to the size of the first region. The term "stylus" does not denote a limitation on the size of the structure, and in some embodiments, it may appear or be in the form of a stylus tip that permanently or retractably extends from or is associated with the tapered tip of the first region.

The devices may optionally contain a plastic or metal loop. The loop may be large enough to thread a carabiner or hook or rope or cord that can be affixed with a backpack, bag, or element of clothing.

Methods

According another embodiment of the present invention, a user may reduce blood flow by wrapping a constricting band 280 around a bleeding limb 290 (bleeding aspect not shown), and associating a device 200 of the present invention with the restricting band, e.g., between wraps of the restricting band. If the constricting band is not in the form of a loop, its ends should be tied after or before placing a portion around a limb in order to create a loop. Twisting of the device may be done until blood flow is reduced a desired amount or stemmed completely. Optionally, the user may secure the device by slipping a clip 240 of tourniquet windlass pen under the constricting band.

In order to secure the restricting band, a user may slide a portion of the fabric 250 along the front side of the housing, past the retaining element. During this process, and while the tourniquet is in use, the portion of the constricting band around the second region of the device may maintain its position there, i.e., not unwind or not unwind to a degree that causes the constricted blood vessel to become undesirably less constricted.

In some embodiments, prior to affixing the clip to the constricting band, the user will have twisted the windlass a sufficient number of times to cause constriction of the blood vessels. The actual number of times will depend on the length and nature of the material that is used as the constricting band and the size of the limb and blood vessels that are sought to be constricted.

Thus, after the blood vessels have been sufficiently constricted, the user may position the clip to be near a portion of the constricting band. He or she may then slide that portion of the constricting band past a nub or other protrusion in the retaining element if present. In some embodiments, during the slide, the fabric may be stretched, and after it is within the cavity, it may be less stretched and thus bunch up and be held in place. The fabric that enters the clip may be a portion from around the limb. Because the size of the space between the housing and the retaining element is smaller than the mouth, the retaining element may prevent the constricting band from sliding out of the mouth.

Unless otherwise specified or apparent from context, any of the features of the various embodiments described herein can be used in conjunction with any other features described in connection with any other embodiments disclosed. Thus, features described in connection with the various or specific embodiments are not to be construed as not suitable in connection with other embodiments disclosed herein unless such exclusivity is explicitly stated or implicit from context.

I claim:

1. A method of reducing flow of blood, said method comprising:
    (a) wrapping a constricting band around a limb;
    (b) associating a tourniquet windlass device with the constricting band, wherein the tourniquet windlass device comprises a clip and a housing, wherein the housing comprises:
        (i) a first region,
        (ii) a second region, wherein the second region has a surface that contains knurling, and
        (iii) a third region, wherein the third region is associated with the clip, wherein the second region is narrower than the widest portion of the first region and narrower than the widest portion of the third region:
    (c) twisting the device, thereby reducing blood flow; and
    (d) securing the constricting band in the clip.

2. The method of claim 1, wherein the tourniquet windlass device further comprises a writing element, wherein the writing element comprises at least one of ink, graphite, lead, and chalk and the writing element is associated with the first region.

3. The method of claim 2, wherein third region has one or both of a left side region, wherein the left side region comprises a section that is planar or concave, or a combination thereof and a right side region, wherein the right side region comprises a section that is planar or concave, or a combination thereof.

4. The method of claim 3, wherein the left side region comprises a section that is planar and the right side region comprises a section that is planar.

5. The method of claim 4, wherein the third region comprises a tapered section, and the tapered section is located between the second region and each of the right side region and the left side region.

6. The method of claim 5, wherein the length of the clip is smaller than the length of the section of the right side region that is planar, concave or a combination thereof and smaller than section of the left side region that is planar, concave or a combination thereof.

7. The method of claim 5 wherein between the clip and a front region of the third region is a cavity that is 20-30 mm deep and 2 mm to 4 mm wide.

8. The method of the claim 4, wherein the second region has a uniform diameter.

9. The method of claim 2, where the writing element further comprises a retractable ink cartridge.

10. The method of claim 1, wherein the third region has a left side region, wherein the left side region comprises a section that is planar or concave, or a combination thereof and a right side region, wherein the right side region is planar or concave, or a combination thereof.

11. The method of claim 10, wherein the section of the left side region that is planar or concave or a combination thereof and the section of the right side region is planar or concave or a combination thereof each are 30% to 80% as long as the third region.

12. The method of claim 10, wherein the length of the clip is smaller than each of the sections of the right side region and the length of the left side region that is planar, concave or a combination thereof.

13. The method of claim 10, wherein the clip extends from the third region and the clip comprises a nub, wherein the nub is located at or near an end of the clip that is distal to where the clip extends from the third region.

14. The method of claim 1, wherein the clip extends from the third region, the clip extends toward the first region, and the clip defines a cavity, wherein the cavity opens toward the first region, and further wherein the clip comprises a retaining element, wherein the retaining element defines a channel between the clip and the third region, wherein the channel is narrower than the width of the cavity, wherein the width of the cavity is a distance between the clip and the third region at a location between the retaining element and the location where the clip extends from the third region and further wherein the second region is located between the first region and the third region and the surface of the second region that contains knurling covers a region that corresponds to the midpoint of the length of the device and wherein the knurling is not present on the surface of the first region and is not present on the surface of the third region.

15. The method of claim 1, wherein said associating comprises looping the constricting band around the windlass device.

16. The method of claim 1 further comprising tying a knot in the constricting band.

17. The method of claim 1, wherein the constricting band comprises fabric.

18. The method of claim 1, wherein the constricting band comprises a rope.

19. The method of claim 1, wherein the constricting band comprises a necktie.

20. The method of claim 1, wherein the constricting band comprises a belt.

* * * * *